(12) United States Patent
Grund et al.

(10) Patent No.: US 8,077,294 B1
(45) Date of Patent: Dec. 13, 2011

(54) OPTICAL AUTOCOVARIANCE LIDAR

(75) Inventors: Christian J. Grund, Boulder, CO (US); Robert M. Pierce, Longmont, CO (US)

(73) Assignee: Ball Aerospace & Technologies Corp., Boulder, CO (US)

( * ) Notice: Subject to any disclaimer, the term of this patent is extended or adjusted under 35 U.S.C. 154(b) by 319 days.

(21) Appl. No.: 12/357,251

(22) Filed: Jan. 21, 2009

Related U.S. Application Data

(60) Provisional application No. 61/021,842, filed on Jan. 17, 2008.

(51) Int. Cl.
*G01C 3/08* (2006.01)
(52) U.S. Cl. .......... 356/4.01; 356/3.01; 356/3.1; 356/4.1
(58) Field of Classification Search ......... 356/3.01–28.5
See application file for complete search history.

(56) References Cited

U.S. PATENT DOCUMENTS

| | | |
|---|---|---|
| 4,022,532 A | 5/1977 | Montagnino |
| 4,201,468 A | 5/1980 | Margolis et al. |
| 5,029,023 A | 7/1991 | Bearden et al. |
| 5,091,778 A | 2/1992 | Keeler |
| 5,192,978 A | 3/1993 | Keeler |
| 5,317,376 A | 5/1994 | Amzajerdi et al. |
| 5,345,304 A | 9/1994 | Allen |
| 5,357,371 A | 10/1994 | Minott |
| 5,485,009 A | 1/1996 | Meyzonnetie et al. |
| 5,682,225 A | 10/1997 | DuBois et al. |
| 5,682,229 A | 10/1997 | Wangler |
| 5,784,023 A | 7/1998 | Bluege |
| 5,793,034 A | 8/1998 | Wesolowicz et al. |
| 5,815,250 A | 9/1998 | Thomson et al. |
| 5,847,816 A | 12/1998 | Zediker et al. |
| 5,870,180 A | 2/1999 | Wangler |
| 5,870,181 A | 2/1999 | Andressen |
| 5,914,776 A | 6/1999 | Streicher |
| 5,917,596 A | 6/1999 | Jenkins et al. |
| 5,923,466 A | 7/1999 | Krause et al. |
| 6,034,770 A | 3/2000 | Kim et al. |
| 6,173,066 B1 | 1/2001 | Peurach et al. |
| 6,323,941 B1 | 11/2001 | Evans et al. |

(Continued)

FOREIGN PATENT DOCUMENTS

GB 2300325 10/1996

(Continued)

OTHER PUBLICATIONS

Brian F. Aull et al., "Geiger-Mode Avalanche Photodiodes for Three-Dimensional Imaging", Lincoln Laboratory Journal, vol. 13, No. 2 (2002).

(Continued)

*Primary Examiner* — Thomas Tarcza
*Assistant Examiner* — Luke Ratcliffe
(74) *Attorney, Agent, or Firm* — Sheridan Ross P.C.

(57) ABSTRACT

Lidar systems and methods are provided. The lidar system includes an optical autocovariance receiver and one or more chemical composition sensors or processors, in addition to a Doppler signal processor for obtaining relative wind speed information. The additional processors may include a high spectral resolution lidar signal processor and/or a differential absorption lidar processor that receive input signals from the optical autocovariance receiver. Receivers that may be incorporated into the lidar system, in addition to the optical autocovariance receiver, include a depolarization receiver, a Raman receiver, and/or an Etalon receiver.

25 Claims, 7 Drawing Sheets

U.S. PATENT DOCUMENTS

| | | |
|---|---|---|
| 6,411,871 B1 | 6/2002 | Lin |
| 6,414,746 B1 | 7/2002 | Stettner et al. |
| 6,434,211 B1 | 8/2002 | Lloyd et al. |
| 6,448,572 B1 | 9/2002 | Tennant et al. |
| 6,542,831 B1 | 4/2003 | Moosmuller et al. |
| 6,608,669 B2 | 8/2003 | Holton et al. |
| 6,646,725 B1 | 11/2003 | Eichinger et al. |
| 6,657,733 B1 | 12/2003 | Drake |
| 6,664,529 B2 | 12/2003 | Pack et al. |
| 6,665,063 B2 | 12/2003 | Jamieson et al. |
| 6,747,258 B2 | 6/2004 | Benz et al. |
| 6,804,607 B1 | 10/2004 | Wood |
| 6,943,868 B2 | 9/2005 | Haig |
| 6,972,887 B2 | 12/2005 | Wickham et al. |
| 7,006,203 B1 | 2/2006 | Book et al. |
| 7,095,488 B2 | 8/2006 | Jamieson et al. |
| 7,113,886 B2 | 9/2006 | West |
| 7,142,981 B2 | 11/2006 | Hablani |
| 7,224,466 B2 | 5/2007 | Ray |
| 7,224,707 B2 | 5/2007 | Gendron |
| 7,236,235 B2 | 6/2007 | Dimsdale |
| 7,240,879 B1 | 7/2007 | Cepollina et al. |
| 7,277,641 B1 | 10/2007 | Gleckman |
| 7,342,228 B1 | 3/2008 | O'Connell et al. |
| 7,345,743 B1 | 3/2008 | Hartman et al. |
| 7,359,057 B2 | 4/2008 | Schwiesow |
| 7,397,568 B2 | 7/2008 | Bryce et al. |
| 7,406,220 B1 | 7/2008 | Christensen et al. |
| 7,436,494 B1 | 10/2008 | Kennedy et al. |
| 7,453,552 B1 | 11/2008 | Miesak |
| 7,580,132 B2 | 8/2009 | Baillon et al. |
| 2002/0117340 A1 | 8/2002 | Stettner |
| 2003/0063884 A1 | 4/2003 | Smith et al. |
| 2004/0021852 A1 | 2/2004 | DeFlumere |
| 2004/0130702 A1 | 7/2004 | Jupp et al. |
| 2005/0060092 A1 | 3/2005 | Hablani |
| 2005/0099634 A1 | 5/2005 | Dubois et al. |
| 2005/0160822 A1* | 7/2005 | Langdon .................. 73/655 |
| 2006/0088946 A1 | 4/2006 | Willson et al. |
| 2006/0114447 A1 | 6/2006 | Harris et al. |
| 2006/0132752 A1 | 6/2006 | Kane |
| 2006/0136172 A1 | 6/2006 | O'Kane et al. |
| 2006/0197936 A1 | 9/2006 | Liebman et al. |
| 2007/0073486 A1 | 3/2007 | Tillotson et al. |
| 2007/0110364 A1 | 5/2007 | Rice et al. |
| 2007/0115541 A1 | 5/2007 | Rogers et al. |
| 2007/0122001 A1 | 5/2007 | Wang et al. |
| 2007/0171407 A1 | 7/2007 | Cole et al. |
| 2007/0263676 A1 | 11/2007 | Beukema et al. |
| 2008/0023587 A1 | 1/2008 | Head et al. |
| 2008/0136626 A1 | 6/2008 | Hudson et al. |
| 2008/0212328 A1 | 9/2008 | Minano et al. |
| 2008/0273560 A1 | 11/2008 | Stelmakh |
| 2008/0290259 A1 | 11/2008 | Mathewson et al. |
| 2008/0316498 A1 | 12/2008 | Drake et al. |
| 2009/0002680 A1 | 1/2009 | Ruff et al. |
| 2009/0046289 A1 | 2/2009 | Caldwell et al. |
| 2009/0110267 A1 | 4/2009 | Zakhor et al. |
| 2009/0115994 A1 | 5/2009 | Stettner et al. |
| 2009/0142066 A1 | 6/2009 | Leclair et al. |
| 2009/0237640 A1 | 9/2009 | Krikorian et al. |
| 2009/0273770 A1 | 11/2009 | Bauhahn et al. |
| 2010/0165323 A1 | 7/2010 | Fiess et al. |

FOREIGN PATENT DOCUMENTS

| | | |
|---|---|---|
| GB | 2306828 | 5/1997 |
| GB | 2364840 | 2/2002 |
| WO | WO 02/04982 | 1/2002 |
| WO | WO 02/065155 | 8/2002 |
| WO | WO 2007/081628 | 7/2007 |
| WO | WO 2009/133414 | 11/2009 |

OTHER PUBLICATIONS

Didier Bruneau, "Mach-Zehnder Interferometer as a Spectral Analyzer for Molecular Doppler Wind Lidar", Applied Optics, vol. 40, No. 3, pp. 391-399 (2001).

Didier Bruneau and Jacques Pelon, "Simulation and Measurement of Particle Backscattering & Extinction Coefficient & Wind Velocity by Lidar with a Mach-Zehnder Interferometer: Principle of Operation & Performance Assessment", Applied Optics, vol. 42, No. 6, pp. 1101-1114 (2003).

Pierre Connes and Guy Michel, "Astronomical Fourier Spectrometer", Applied Optics, vol. 14, No. 9, pp. 2067-2084 (1975).

Degnan, John J., "Photon-Counting Multikilohertz Microlaser Altimeters for Airborne and Spaceborne Topographic Measurements", Journal of Geodynamics, vol. 34, pp. 503-549 (2002).

T.S. Durrani and C.A. Greated, "Spectral Analysis and Cross-Correlation Techniques for Photon Counting Measurements on Fluid Flows", Applied Optics, vol. 14, No. 3, pp. 778-794 (1975).

W.A. Gault, et al., "Erwin: An E-Region Wind Interferometer", Applied Optics, vol. 35, No. 16, pp. 2913-2922 (1996).

Gentry, Bruce et al., "The Tropospheric Wind Lidar Technology Experiment (TWiLiTE): An Airborne Direct Detection Doppler Lidar Instrument Development Program", available at http://esto.nasa.gov/conferences/estc2006/papers/b8p2.pdf.

Pierre Jacquinot, "*The Luminosity of Spectrometers with Prisms, Gratings, or Fabry-Perot Etalons*", Journal of the Optical Society of America, vol. 44, No. 10, pp. 761-765 (1954).

V. Nirmal Kumar and D. Narayana Rao, "*Determination of the Instrument Function of a Grating Spectrometer by Using White-Light Interferometry*", Applied Optics, vol. 36, No. 19, pp. 4535-4539 (1997).

Lieber, Mike et al., "Development of a Validated End-to-End Model for Space-Based Lidar Systems", *Lidar Remote Sensing for Environmental Monitoring VIII* (Singh, Upendra N. ed.), Proceedings of the SPIE, vol. 6681, 66810F (2007).

Lieber, Mike et al., "System Verification of the JMEX Mission Residual Motion Requirements with Integrated Modeling", *UV/Optical/IR Space Telescopes: Innovative Technologies and Concepts II* (MacEwen, Howard A. ed.), Proceedings of the SPIE, vol. 5899, 589901, pp. 1-12 (2005).

Lieber, Mike et al., "Integrated System Modeling for Evaluating the Coronagraph Approach to Plant Detection", *High-Contrast Imaging for Exo-Planet Detection* (Schultz, Alfred B. ed.), Proceedings of the SPIE, vol. 4860 (2002). (Abstract only).

W.T. Mayo, Jr., "Photon Counting Processor for Laser Velocimetry", Applied Optics, vol. 16, No. 5, pp. 1157-1162 (1977).

G.A. Morton, "Photon Counting", Applied Optics, vol. 7, No. 1, pp. 1-10 (1968).

Rabinovich, W.S. et al., "45 Mbps Cat's Eye Modulating Retro-Reflector Link Over 7 Km", *Free-Space Laser Communications VI*, Proceedings of the SPIE, vol. 6304, pp. 63040Q (2006). (Abstract only).

Robert L. Richardson and Peter R. Griffiths, "Design and Performance Considerations of Cat's Eye Retroreflectors for Use in Open-Path Fourier-Transform-Infrared Spectrometry", Applied Optics, vol. 41, No. 30, pp. 6332-6340 (2002).

J. Ring and J.W. Schofield, "Field-Compensated Michelson Spectrometers", Applied Optics, vol. 11, No. 3, pp. 507-516 (1972).

Gordon G. Shepherd et al., "WAMDII: Wide-Angle Michelson Doppler Imaging Interferometer for Spacelab", Applied Optics, vol. 24, No. 11, pp. 1571-1584 (1985).

Gordon G. Shepherd et al., "WINDII—The Wind Imaging Interferometer for the Upper Atmosphere Research Satellite", Geophys. Res. vol. 98, No. D6, pp. 10,725-10,750 (1993).

Vallerga, John et al., "Noiseless, High Frame Rate (>KHz), Photon Counting Arrays for Use in the Optical to the Extreme UV", University of California, Berkeley—Sciences Laboratory and University of Geneva, Switzerland, available at http://www.ssl.berkeley.edu/~mcphate/AO/ao_medipix.html (2004-present).

Shiquang Wang, Gordon G. Sheperd, and William E. Ward, "Optimized Reflective Wide-Angle Michelson Phase-Stepping Interferometer", Applied Optics, vol. 39, No. 28, pp. 5147-5160, (2000).

Grund, et al. "Enabling Characteristics of Optical Autocovariance Lidar for Global Wind and Aerosol Profiling", AGU, American Geophysical Union, Fall Meeting, San Francisco, CA (Dec. 16, 2008).

Grund, Chris, "An Alternative Direct Detection Approach to Doppler Winds that is Independent of Aerosol Mixing Ratio and Transmitter Frequency Jitter", Space Winds Lidar Working Group, Miami, FL (Feb. 8, 2007).

Grund, Christian et al., "Optical Autocovariance Wind Lidar and Performance from LEO", 14th Coherent Laser Radar Conference, Snowmass, CO (Jul. 7, 2007).

Grund, Christian et al., "Supporting NOAA and NASA High-Performance Space-Based DWL Measurement Objectives with a Minimum Cost, Mass, Power, and Risk Approach Employing Optical Autocovariance Wind Lidar (OAWL)", Space Winds Lidar Working Group, Monterrey, CA (Feb. 6, 2008).

Grund, Christian, et al., "Simultaneous Profiling of Aerosol Optical Properties, Gas Chemistry, and Winds with Optical Autocovariance Lidar", 24th ILRC Conference (Jun. 23, 2008).

Chris Grund, "Lidar Wind Profiling from Geostationary Orbit Using Imaging Optical Autocovariance Interferometry", Space Winds Lidar Working Group, Snowmass, CO (Jul. 17, 2007).

Grund, et al., "Optical Autocovariance Wind Lidar (OAWL) for Efficient Space-Based Direct-Detection High-Resolution Aerosol Backscatter Winds", International Laser Radar Conference, Boulder, CO (Jun. 24, 2008).

U.S. Appl. No. 12/390,226, filed Feb. 20, 2009.

U.S. Appl. No. 12/357,171, filed Jan. 21, 2009.

Allen et al., "Full-Scale Testing and Platform Stabilization of a Scanning Lidar System for Planetary Landing", *Space Exploration Technologies* (Wolfgang Fink, ed.), Proceedings of SPIE, vol. 6960, pp. 696004-1-696004-10 (2008).

Bakalski et al., "Real Time Processing Enables Fast 3D Imaging at Single Photon Level", *Laser Radar Technology and Applications XIII*, (Monte D. Turner, Gary W. Kamerman, ed.), Proceedings of the SPIE, vol. 6950, pp. 69500K-1-69500K-9 (2008).

Baker et al., "Advanced Infrared Detectors for Multimode Active and Passive Imaging Applications" *Infrared Technologies and Applications XXXIV* (Bjorn F. Andresen, Gabor F. Fulop, and Paul R. Norton, ed.), Proceedings of the SPIE, vol. 6940, pp. 69402L-1-69402L-11 (2008).

Brady and Schwartz, "ALHAT System Architecture and Operational Concept", Aerospace Conference, 2007 IEEE, Big Sky, MT, IEEEAC Paper # 1570, Version 4, pp. 1-13 (2007).

Cho et al., "Real-Time 3D Ladar Imaging", 35th Applied Imagery and Patern Recognition Workshop, pp. 5 (2006).

Craig et al., "Processing 3D Flash LADAR Point-Clouds in Real-Time for Flight Applications", *Sensors and Systems for Space Applications* (Richard T. Howard and Robert D. Richards, ed.), Proceedings of SPIE, vol. 6555, pp. 65550D-1-65550D-9 (2007).

Dissly et al., "Flash LIDAR Systems for Planetary Exploration", American Astronomical Society, DPS Meeting, Presentation # 40, Ithaca, NY, Bulletin of the American Astronoimical Society, vol. 41, pp. 560 (2008).

Fay et al., "Fusion of Multi-Sensor Pasive and Active 3D Imagery", *Enhanced and Synthetic Vision 2001* (Jacques G. Verly, ed.), Proceedings of SPIE, vol. 4363, pp. 219-230 (2001).

Gillula, "Data Fusion From Multiple Sensors: Real-Time Mapping on an Unmanned Ground Vehicle", 2005 SURF Final Report, California Institute of Technology, 13 pgs (2005).

Habbit et al., "Utilization of Flash LADAR for Cooperative and Uncooperative Rendezvous and Capture", Space Systems Technology and Operations (Peter Tchoryk, Jr. And James Shoemaker, ed.), Proceedings of SPIE, vol. 5088, pp. 146-157 (2003).

Hyde et al., "Mapping Forest Structure for Wildlife Habitat Analysis Using Multi-Sensor (LiDAR, SAR/InSAR, ETM+, Quickbird) Synergy", Remote Sensing of Environment, vol. 102, pp. 63-73 (2006).

De Lafontaine et al., "LAPS: The Development of a Scanning Lidar System with GNC for Autonomous Hazard Avoidance and Precision Landing"; *Spaceborne Sensors* (Robert D. Habbit, Jr. and Peter Tchoryk, Jr., ed.), Proceedings of SPIE, vol. 5418, pp. 81-93 (2004).

Lamoreux et al., "Relative Navigation Sensor for Autonomous Rendezvous and Docking", *Laser Radar Technology and Applications VIII* (Gary W. Kamerman, ed.), Proceedings of the SPIE, vol. 5086, pp. 317-328 (2003).

Lefsky et al., "Estimates of Forest Canopy Height and Aboveground Biomass Using ICESat", Geophysical Research Letters, vol. 32, L2202, 4 pages (2005).

Marino and Davis, Jr., "Jigsaw: A Foliage-Penetrating 3D Imaging Laser Radar System"; Lincoln Laboratory Journal, vol. 15, No. 1, pp. 23-36 (2005).

Oberle and Davis, "Toward High Resolution, Ladar-Quality 3-D World Models Using Ladar-Stereo Data Integration and Fusion," Army Research Laboratory, ARL-TR-3407, 37 pgs (2005).

Pack et al., "A Co-Boresighted Synchronized Ladar/EO Imager for Creating 3D Images of Dynamic Scences", *Laser Radar Technology and Applications, X* (Gary W. Kamerman, ed.), Proceedings of SPIE, vol. 5791, pp. 42-50 (2005).

Pierrottet et al., "Characterization of 3-D Imaging Lidar for Hazard Avoidance and Autonomous Landing on the Moon"; *Laser Radar Technology and Applications XII* (Monte D. Turner and Gary W. Kamerman, ed.), Proceedings of SPIE, vol. 6550, pp. 655008-1-655008-9 (2007).

Riris et al., "The Lunar Orbiter Laser Altimeter (LOLA) on Nasa's Lunar Reconnaissance Orbiter (LRO) Mission", *Sensors and Systems for Space Applications* (Richard T. Howard and Robert D. Richards, ed.), Proceedings of SPIE, vol. 6555, pp. 655501-1-655501-8 (2007).

Roberts, Jr. and LeVan, "Aperture Sharing Between Low-Background Infrared Sensors and Ladar Sensors", Aerospace Applications Conference, Proceedings of the IEEE, vol. 4, pp. 495-508 (1996).

Smith et al., "Diffractive Optics for Moon Topography Mapping"; *Micro (MEMS) and Nanotechnologies for Space Applications* (Thomas George and Zhong-Yang Cheng, ed.), Proceedings of SPIE, vol. 6223, pp. 622304-1-622304-10 (2006).

Stentz et al., "Real-Time, Multi-Perspective Perception for Unmanned Ground Vehicles", Proceedings of the Association for Unmanned Vehicle Systems International, 15 pgs (2003).

Tan and Narayanan, "Design and Performance of a Multiwavelength Airborne Polarimetric Lidar for Vegetation Remote Sensing"; Journal of Applied Optics, vol. 43, No. 11, pp. 2360-2368 (2004).

Trenkle et al., "3D Sensor Algorithms for Spacecraft Pose Determination", *Spaceborne Sensors III* (Richard T Howard and Robert D. Richards, ed.), Proceedings of SPIE, vol. 6220, pp. 62200D-1-62200D-14 (2006).

Weinberg et al., "Flash Lidar Systems for Hazard Detection, Surface Navigation and Autonomous Rendezvous and Docking", 2007 LEAG Workshop on Enabling Exploration, 2 pgs (2007).

Yoon et al., "High Frequency Attitude Motion of ICESat", *Advances in Astronautical Sciences* (David A. Vollado, Michael J. Gabor and Prasun N. Desai ed.), vol. 120: Spaceflight Mechanics, Part 1, pp. 117-131 (2005).

Robert C. Fenton, "A LADAR-Based Pose Estimation Algorithm for Determining Relative Motion of a Spacecraft for Autonomous Rendezvous and Dock", Master of Science thesis, Utah State University, 90 pages (2008).

Chen et al., "RANSAC-Based DARCES: A New Approach to Fast Automatic Registration of Partially Overlapping Range Images", IEEE Transactions on Pattern Analysis and Machine Intelligence, vol. 21, No. 11, 6 pages (Nov. 1999).

Vasile et al., "Pose-Independent Automatic Target Detection and Recognition Using 3D Laser Radar Imagery", Lincoln Laboratory Journal, vol. 15, No. 1, 18 pages (2005).

Ruel et al., "Field Testing of a 3D Automatic Target Recognition and Pose Estimation Algorithm", Automatic Target Recognition XIV, SPIE vol. 5426, 10 pages (2004).

Allen et al., "Rendezvous Lidar Sensor System for Terminal Rendezvous, Capture, and Berthing to the International Space Station", Sensors and Systems for Space Applications II, SPIE vol. 6958, 8 pages (2008).

Jasiobedzki et al., "Autonomous Satellite Rendezvous and Docking Using LIDAR and Model Based Vision", Spaceborne Sensors II, SPIE vol. 5798, 12 pages (2005).

Fenton et al., "Simulation Tests of a Lidar-based Spacecraft Pose Determination Algorithm", Sensors and Systems for Space Applications, SPIE vol. 6555, 11 pages (2007).

Ruel et al., "Real-Time 3D Vision Solution for On-Orbit Autonomous Rendezvous & Docking", Spaceborne Sensors III, SPIE 6220, 11 pages (2006).

Trenkle et al., "3-D Sensor Algorithms for Spacecraft Pose Determination", Spaceborne Sensors III, SPIE vol. 6220, 14 pages (2006).

Wikipedia, "RANSAC", available at http://en.wikipedia.org/wiki/RANSAC, 5 pages (2009).

Examiner Copenheaver, International Search Report and Written Opinion for International Patent Application No. PCT/US2010/021213, mailed Mar. 22, 2010, 8 pages.

Kasten, et al., "Fabrication and Characterization of Individually Addressable Vertical-Cavity Surface-Emitting Laser Arrays and Integrated VCSEL/PIN Detector Arrays", Proceedings of SPIE, vol. 6484, 64840C, 2007.

Aerius Photonics website, "Aerius NIR/SWIR Illuminators" product sheet, available at http://www.aeriusphotonics.com/datasheets.html, 2 pages (2009).

US PTO Office Action for U.S. Appl. No. 12/464,009 mailed Aug. 4, 2010, 16 pages.

International Search Report and Written Opinion for International Patent Application Serial No. PCT/US2010/033559, mailed Jul. 6, 2010, 9 pages.

U.S. Appl. No. 12/464,009 filed May 11, 2009.

U.S. Appl. No. 12/857,354 filed Aug. 16, 2010.

Notice of Allowance and Fee(s) Due for U.S. Appl. No. 12/390,226, mailed Dec. 17, 2010, 23 pages.

Notice of Allowance and Fee(s) Due for U.S. Appl. No. 12/464,009, mailed Jan. 31, 2011, 10 pages.

Grund et al., Poster Entitled "Optical Autocovariance Wind Lidar (OAWL) for Efficient Space-Based Direct-Detection High-Resolution Aerosol Backscatter Winds", presented at the Coherent Laser Radar Conference, Jul. 2007, presented at the Working Group on Space-based Lidar Winds, Feb. 2008, and presented at the International Laser Radar Conference in Boulder, Jun. 23-27, 2008, 1 page.

Grund, Christian J., Power Point Presentation Entitled "Optical Autocovariance: Alternative Direct Detection Approach to Doppler Winds that is Independent of Aerosol Mixing Ratio and Transmitter Frequency Jitter", presented at the Working Group Conference on Space-Based Lidar Winds, Feb. 6-9, 2007, 12 pages.

Grund et al., Presentation Entitled "Optical Autocovariance Wind Lidar and Performance from LEO", presented at the Coherent Laser Radar Conference, Jul. 11, 2007, 30 pages.

Grund et al., "Simultaneous Profiling of Aerosol Optical Properties, Gas Chemistry, and Winds with Optical Autocovariance Lidar", Paper 1 of 2 presented at the 24th International Laser Radar Conference, Jun. 23-27, 2008, 5 pages.

Grund et al., "Optical Autocovariance Wind Lidar (OAWL) for Efficient Space-Based Direct-Detection High-Resolution Aerosol Backscatter Winds", Paper 2 of 2 presented at the 24th International Laser Radar Conference, Jun. 23-27, 2008, 5 pages.

* cited by examiner

OPTICAL AUTOCOVARIANCE LIDAR

CROSS REFERENCE TO RELATED APPLICATIONS

This application claims the benefit of U.S. Provisional Patent Application Ser. No. 61/021,842, filed Jan. 17, 2008, the entire disclosure of which is hereby incorporated herein by reference.

FIELD

A lidar system incorporating an optical autocovariance lidar receiver is provided. More particularly, an optical autocovariance lidar is provided that can be used in combination with a variety of different instruments that receive input from a common telescope.

BACKGROUND

Light detection and ranging (LIDAR) systems have been developed that, in addition to range measurements, are capable of remotely measuring winds in connection with weather forecasting and climate studies, and relative velocities of hard targets in connection with target identification and threat assessment. Lidar systems have also been used in connection with remote sensing of chemical compounds, gasses, and aerosol optical properties in the atmosphere, and surface chemistry and physical properties of hard targets. In general lidar operates by transmitting light from a laser source to a volume or surface of interest and detecting the time of flight for the backscattered light to determine range to the scattering volume or surface.

A Doppler wind lidar additionally measures the Doppler shift experienced by photons scattered back to the instrument due to the motions of molecules and aerosols (e.g. particles and droplets) in the scattering volumes. The speed of the wind is determined from the line of sight (LOS) speed of the molecules and aerosols relative to the lidar. However, such systems have been limited to taking brief snapshots of wind speed over relatively small areas. In addition, the range of such systems has been limited, because of the small number of photons that are returned to a detector when ranges are large. As a result, lidar systems placed in low earth orbit (LEO) are relatively close to the surface and therefore travel at a significant speed relative to the surface of the Earth, limiting their ability to economically collect data with the spatial and temporal coverage needed for various environmental and defense applications.

The remote sensing of chemicals in the atmosphere can be accomplished using differential absorption lidar (DIAL). In a DIAL system, light at different wavelengths is transmitted across a volume of interest, and the strength of the backscatter intensity from subsequent volume or surface backscatter is used to determine the relative attenuation across the volume in order to identify those wavelengths that are absorbed by the compounds in that volume of interest and their relative concentrations. Accordingly, the system must be capable of operating at a number of different wavelengths. However, such frequency hopping has made simultaneous wind lidar measurements difficult or impossible with traditional Doppler Wind Lidar methods, particularly using a common, integrated instrument. As a result, measurements of wind have been made separately from chemistry measurements, resulting in chemical flux measurements that are highly susceptible to errors due to temporal and spatial sampling discrepancies. In addition, variations in the aerosol backscatter and extinction properties either spectrally or spatially within the measurement volume leads to additional errors in DIAL measurements.

Another technique for sensing the chemistry and other features, such as temperature and pressure, of volumes in the atmosphere or other target volumes include Raman lidar. However, as with DIAL systems, Raman lidar has only been possible using systems that are separate from a Doppler wind lidar. Accordingly, the difficulties with flux measurements mentioned above in connection with DIAL instruments have also been present in connection with HSRL and Raman lidar systems.

SUMMARY

The present invention is directed to solving these and other problems and disadvantages of the prior art. In accordance with embodiments of the present invention, an optical autocovariance lidar is provided as part of an integrated lidar system having a number of instruments in addition to the optical autocovariance lidar. The optical autocovariance lidar and the additional instrument or instruments share a common receiver telescope. In addition, the optical autocovariance lidar and the other instrument or instruments can share a common laser or set of lasers. This architecture exploits the unique properties of the optical autocovariance wind lidar that allows multiple instrument functions to be performed without loss in efficiency due to signal division. The integration provided by embodiments of the present invention can further yield more accurate measurements of environmental parameters of interest, because those measurements can be performed simultaneously, and are taken from the same target volume. The high degree of integration enabled by the optical autocovariance wind lidar system also leads to efficiencies in system power, mass, and volume that are significant factors for lidar space missions.

In accordance with embodiments of the present invention, laser light backscattered from a volume of interest is provided to an optical autocovariance receiver. The various components of the autocovariance function signal obtained by the optical autocovariance receiver are used to derive line of sight wind speeds. Simultaneously, information regarding the composition of the volume of interest can be obtained. For instance, information regarding the aerosol composition of the volume of interest can be obtained by a high spectral resolution lidar (HSRL) signal processor, and/or a differential absorption lidar (DIAL) signal processor operating in conjunction with and that receive input from the optical autocovariance receiver. As a further example, information regarding the composition of the volume of interest can be obtained using a Raman receiver and Raman signal processor that shares a laser source and receiving telescope with the optical autocovariance receiver. As yet another example, a double edge Etalon receiver can be included in the lidar system. The double edge Etalon receiver can be used to filter light provided to the optical autocovariance receiver, such that the optical autocovariance receiver measures the spectral peak of the central aerosol component of the backscatter return spectrum to which the Etalon is tuned. A depolarization receiver can also be combined with the optical autocovariance receiver, to obtain information regarding the ice/water state of cloud particles, and the surface roughness and other identifying characteristics of hard target surfaces.

The optical autocovariance lidar may be implemented using various techniques. For example, a received signal can be subjected to different path lengths using a stepped mirror in an arm of the optical autocovariance receiver's interferometer. As a further example, the different path lengths can be obtained by introducing different delays to the receive signal. As yet another example, differential polarization can be used to separate a received signal and subject different portions of that signal to different path lengths. In addition, the optical autocovariance receiver can incorporate field widening optics.

Additional features and advantages of embodiments of the present invention will become more readily apparent from the following description, particularly when taken together with the accompanying drawings.

DETAILED DESCRIPTION

Figure 1:
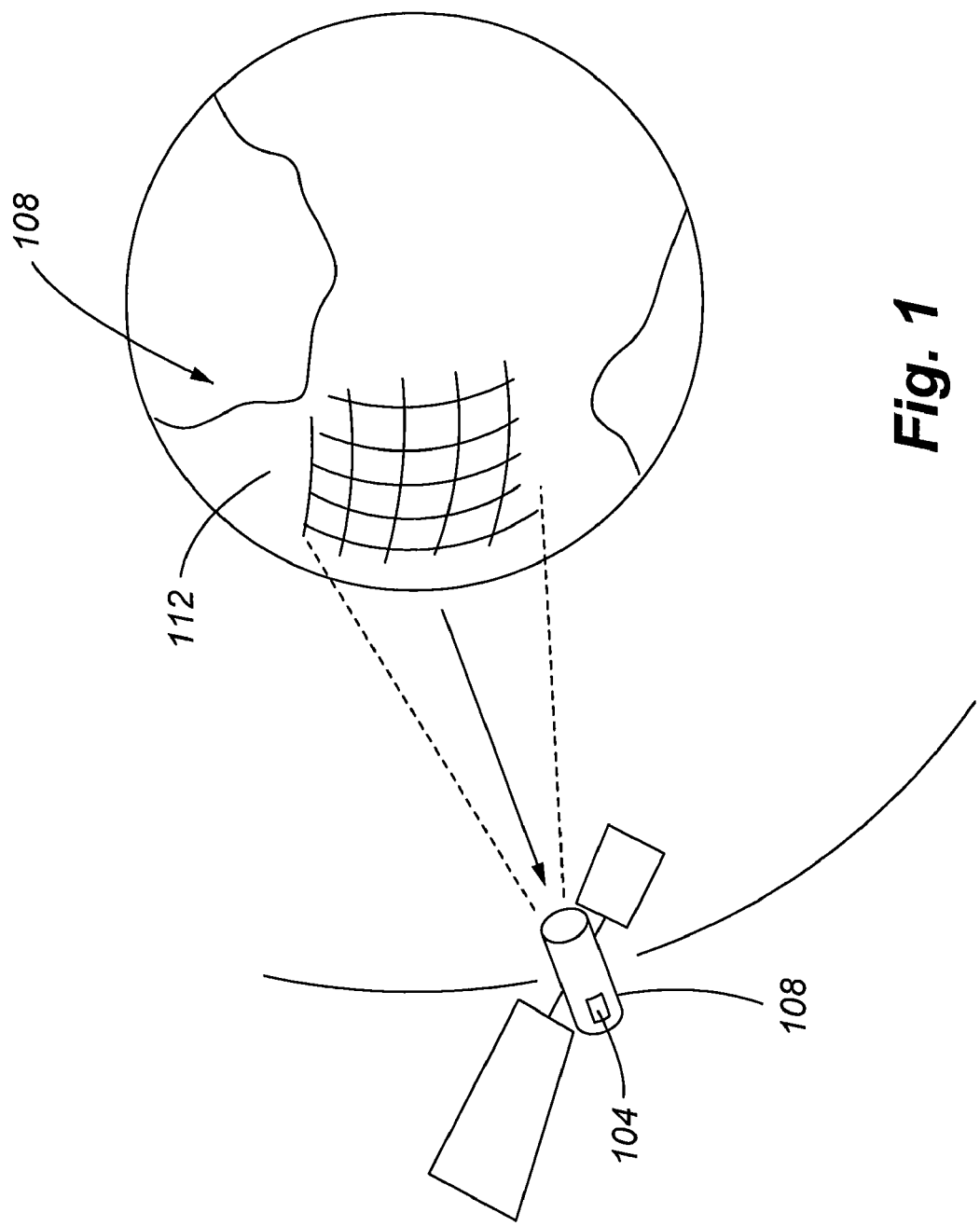
FIG. 1 is a depiction of a lidar system and an associated observation area in accordance with embodiments of the present invention.

FIG. 1 depicts a satellite 100 incorporating a lidar system 104 in accordance with embodiments of the present invention. In addition, an observation area 108 of the lidar system 104, and a target or target volume 112 entirely or partially within the observation area 108, are depicted. As shown, the satellite 100 carrying the lidar system 104 can, in accordance with embodiments of the present invention, be placed in a geosynchronous earth orbit (GEO). Although this is one application of embodiments of the present invention, other applications may include placing a lidar system 104 in satellites at other orbits, in space vehicles, or in air or ground vehicles or locations.

Figure 2:
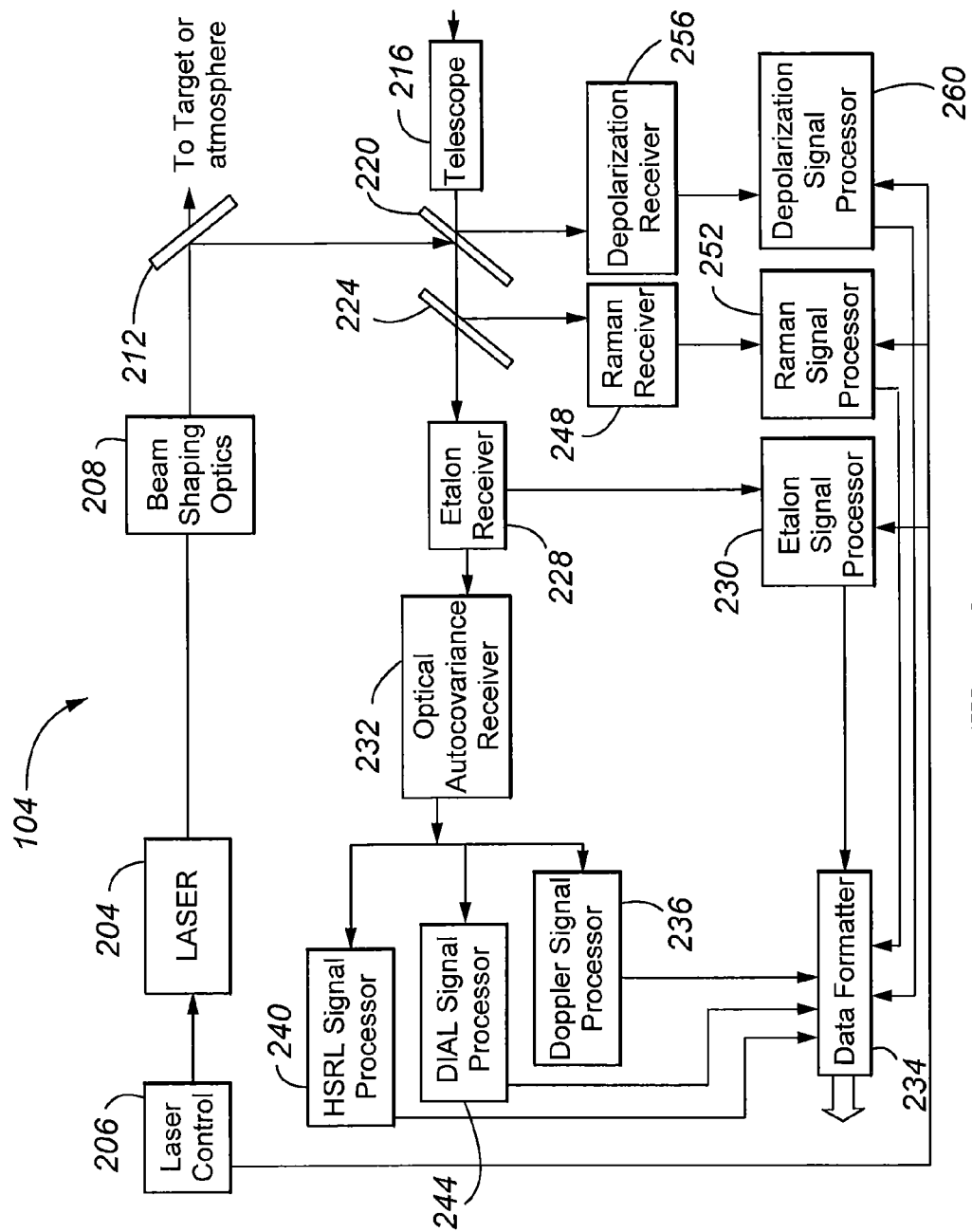
FIG. 2 is a depiction of components of a lidar system in accordance with embodiments of the present invention.

FIG. 2 illustrates components that may be included in a lidar system 104 in accordance with embodiments of the present invention. The lidar system 104 uses the advantages of the optical autocovariance technique alone and in conjunction with other backscatter signal attributes to implement range resolved measurements of molecular and aerosol Doppler winds, calibrated aerosol optical properties, aerosol depolarization properties, atmospheric and surface chemistry, surface vibrometry, and/or thermodynamics. A laser 204, such as a single longitudinal mode laser, generates light that is transmitted toward a remote target via beam shaping optics 208. Multiple lasers 204 that may generate light at the fundamental wavelength and frequency multiples, including solid state, diode, fiber, gas, and dye lasers, which may include sum and difference frequency generators, optical parametric oscillators and amplifiers, and laser amplifiers including fiber amplifiers, can be incorporated into the lidar system 104, for example for illumination of targets using a plurality of different wavelengths. The output of the single laser or multiple lasers 204 can be controlled by a laser control 206. The output from the laser 204 may be passed through a beam sampler 212 to provide a sample of the transmitted wavelength to instruments included in the lidar system 104.

Light reflected from the target 112 is received by a telescope 216. The returned light collected by the telescope 216 is then made available to the instruments included in the lidar system 104. For example, the light collected by the telescope 216 may be passed to a polarizing beam splitter 220. The polarizing beam splitter 220 passes light having the same polarization as the light transmitted to the target, and reflects light having the orthogonal polarization. The polarizing beam splitter 220 also reflects a zero time laser sample that is provided to the polarizing beam splitter 220 by the beam sampler 212 into the beam path, coded in the orthogonal polarization to the receive light. The sample of the light transmitted from the laser 204 provides a spectral calibration signal for each laser pulse that can be used by the multiple receivers and other components of the lidar system 104.

The light passed by the polarizing beam splitter 220 is received by a dichroic mirror 224 that passes the center of the return spectrum and reflects wavelengths displaced from the center wavelength by more than the width of the Doppler broadened molecular spectrum plus the Doppler shift of the return due to relative motion between the lidar system 104 and the target. The light passed by the dichroic mirror 224 may be provided to an Etalon receiver 228. The Etalon receiver 228 can be used to measure the mean Doppler shift of the center of the Doppler broadened molecular backscatter spectrum, to obtain wind speed in situations where molecular backscatter dominates over aerosol backscatter in the total backscatter return. In particular, data collected by the Etalon receiver 228 can be provided to an Etalon signal processor 230 to determine the mean Doppler shift where molecular backscatter dominates over aerosol backscatter. This information can be provided to a data formatter 234 for storage and/or output. The light rejected (i.e., passed out of) the Etalon receiver 228 comprises primarily the center of the backscatter spectrum dominated by the aerosol backscatter when present. Although the optical autocovariance receiver 232 can measure Doppler shifts from both aerosol and molecular backscatter simultaneously, the optimal optical path difference for best performance on each type of backscatter signal is different. The unique combination of an etalon double-edge Doppler receiver with an optical autocovariance receiver allows simultaneous optimization of performance for both aerosol laden and clear air atmospheric conditions.

The lidar system 104 includes an optical autocovariance receiver 232. The optical autocovariance receiver 232 can be used to determine the precise optical frequency of the return light, to measure the Doppler shift of the central frequency due to relative motion between the lidar 104 and the target that reflected the received light. The input to the optical autocovariance receiver 232 can be the light rejected by the Etalon receiver 228. Alternatively, for example where an Etalon receiver 228 is not included in the lidar system 104, or as a further example, where a provided Etalon receiver 228 has been switched out of the path of received light or is provided with light separately, the optical autocovariance receiver 232 may receive light that has not been processed by an Etalon receiver 228. In general, the optical autocovariance receiver 232 provides signals that are processed into representative velocity signals by a Doppler signal processor 236. More particularly, the optical autocovariance receiver 232 comprises an interferometer in which interference signals at slightly different relative optical delays are generated to determine the amplitude of the optical ACF at corresponding optical ACF phase positions. The Doppler signal processor 236 then implements an algorithm that uses signals from the optical autocovariance receiver 232 comprising information regarding the phase shift of the autocovariance function to obtain a frequency shift, which turn allows the relative velocity of the target to be determined. In accordance with embodiments of the present invention, the wind velocity V is calculated from the difference in the optical autocovariance phase ($\Delta\Phi$) between the 0-velocity sample captured by locally sampling the outgoing transmission or pulse from the laser 204 and each range return as follows: $V=\lambda*\Delta\Phi*c/(2*OPD)$, where $\Delta\Phi$ is expressed as a fraction of one optical autocovariance function period, and c is the speed of light. The Doppler signal processor 236 can also function to obtain range (R) information corresponding to velocity measurements from the time delay ($\Delta t$) between the transmitted and backscattered signals giving rise to the optical ACF measurements as follows: $R=c\Delta t/2$. The velocity signals and range information can be provided to the data formatter 234 for storage and/or output.

The signals from the optical autocovariance receiver 232 may also be provided to a high spectral resolution lidar (HSRL) processor 240 to retrieve profiles of calibrated aerosol optical properties, such as particle extinction cross section, backscatter cross section, and backscatter phase function. Accordingly, when operable at several wavelengths, the same information that is used to determine relative wind velocity in a target volume can also be used to determine the wavelength dependence of aerosol optical properties in the target volume, a critical parameter for climate and radiation balance studies. The signals from the HSRL processor can be provided to the data formatter 234 for storage and/or output.

Chemical species measurements (e.g. of $H_2O_v$, $CO_2$, CO, hydrocarbons, chemical agents, etc.) of a target volume can also be obtained using the differential absorption lidar (DIAL) method. In order to apply the DIAL method, a laser 204 that is operable at more than one wavelength, or a plurality of lasers 204 operable at different wavelengths, can be used to provide more than one wavelength, either simultaneously or sequentially. At least two wavelengths are chosen; one coincides with an absorption line of a specific surface coating or atmospheric component, and a second that is substantially less affected by the coating or atmospheric component. The absorption information can be collected by the optical autocovariance receiver 232, and that information can be provided to a DIAL signal processor 244 to obtain an output comprising the results of the chemical species measurements. When simultaneous laser transmitters at multiple wavelengths are employed, the independent wavelength signals can be separated using several methods known in the art. For example, each wavelength transmission can be modulated with a different orthogonal code in the case of pseudo-random noise code modulation ranging. In the case of simple pulsed laser transmitters, the received wavelength signals can be separated by diffraction gratings or dichroic mirrors and captured on separate sets of detectors for each wavelength. Accordingly, such chemical species measurements and wind measurements can be obtained simultaneously, using the hardware associated with the optical autocovariance receiver 232. In particular, DIAL signal processing can be performed in association with or by the optical autocovariance receiver 232, because the aliasing property of the optical autocovariance lidar method allows frequency hopping without affecting performance, provided the zero phase sample is measured and the Doppler shift is determined from the differential optical autocovariance function phase shift between the zero phase measurement and the return. Accordingly, the complex optical wavelength tracking systems required by other coherent and direct detection wind measurement devices are avoided. The output from the DIAL signal processor 244 can be provided to the data formatter 234 for storage and/or output.

The lidar system 104 may also incorporate a Raman receiver 248. The Raman receiver 248 may be provided with a return signal collected by the telescope 216 by the dichroic mirror 224. The Raman receiver 248 may provide an output to a Raman signal processor 252, which can provide chemical composition and a profile of the molecular backscatter cross section to the data formatter 234. As can be appreciated by one of skill in the art, choosing the wavelength of the signal output by the laser 204 to be in the range from the ultraviolet to the near infrared wavelengths facilitates collection of the Raman signal, because Raman backscatter cross section is proportional to wavelength$^{-4}$. Accordingly, the Raman signal processor may communicate with the laser control 206, so that information regarding the wavelength of the signal being output by the laser 204 for a particular laser shot can be exchanged. Because the Raman receiver 248 and the optical autocovariance receiver 232 are simultaneously provided with a signal from the telescope 216, Raman signals gathered for chemical species can be measured at the same time that wind measurements are made by the optical autocovariance receiver 232, and during frequency shifting DIAL signal acquisition. The common measurement path thus provided simplifies coordination of spatial and temporal sampling, reducing measurement errors in system complexity. In addition, it should be noted that the optical autocovariance receiver 232, because it is capable of operating at any of a wide range of wavelengths, can continue to obtain wind measurements even as different wavelengths are transmitted by the laser 204 as part of the collection of signals by the Raman receiver 248. It is further noted that Rayleigh and Raman backscatter intensities both scale with wavelength$^{-4}$. Consequently, optical autocovariance wind measurements from ever-present molecular backscatter and Raman measurements of atmospheric thermodynamics or species density, are mutually enhanced by operations at the shortest wavelength consistent with extinction over the desired maximum range of regard.

The lidar system 104 can also include a depolarization receiver 256 and an associated depolarization signal processor 260. The depolarization receiver 256 can be provided with the orthogonal polarization components of the received spectrum by the polarizing beam splitter 220. The depolarization receiver 256 detects the intensities of the depolarized return components at the various operational wavelengths. The non-depolarized components are proportional to the sum of the corresponding optical autocovariance receiver 232 detector signals. The depolarization ratio is calculated as the quotient of the depolarization signal divided by the sum of the depolarized and non-depolarized components, all corrected for systematic transmission losses, thus allowing simultaneous wind and depolarization lidar profiling without sacrifice of performance in any of the measurements. Such depolarization signals are useful for determining the ice/water state of cloud particles, and the surface roughness and other identifying characteristics of hard surface targets. Because the depolarization receiver 256 detects intensities of the depolarized return at different operational wavelengths, the depolarization signal processor 260 may receive information regarding the wavelength of a particular laser shot from the laser control 206. Information obtained by the depolarization receiver 256 may be output by the depolarization signal processor 260 and provided to the data formatter 234.

As can be appreciated by one of skill in the art, the various processors 230, 236, 240, 244, 252 and 260 can be implemented as different algorithms or processes running on a common processor. Accordingly, a processor dedicated to a particular process or task is not required. As an example, a common processor in the form of a general purpose programmable processor may be provided and operated in cooperation with memory and/or data storage containing instructions comprising the algorithms. These components may be provided as part of a general purpose computer or central processing unit. As further examples, some or all of the included processors 230, 236, 240, 244, 252 and 260 can be implemented as a controller or application specific integrated circuit. Components providing processors 230, 236, 240, 244, 252 and/or 260 can also provide data formatter 234 functions.

Therefore, a lidar system 104 with an optical autocovariance receiver 232 and one or more chemical composition, aerosol, molecular Doppler, or chemical characteristic sensors (e.g., an Etalon receiver, an HSRL signal processor 240, a DIAL signal processor 244, a Raman receiver 248, and/or a depolarization receiver 256) may be provided. Moreover, as illustrated in FIG. 2, a lidar system 104 may include an optical autocovariance receiver 232 and chemical composition or chemical characteristic sensors comprising an HSRL signal processor 240 and/or a DIAL signal processor 244, without requiring hardware in addition to the hardware included as part of the optical autocovariance receiver 232, and those other components of the lidar system 104 necessary for an optical autocovariance lidar. Alternatively or in addition, hardware components, such as an Etalon receiver 228, a Raman receiver 248, and/or a depolarization receiver 256 can be included and operated simultaneously with the optical autocovariance receiver 232 and processors (e.g., processors 236, 240 or 244) associated with the optical autocovariance receiver 232. Accordingly, a lidar system 104 in accordance with embodiments of the present invention enables direct measure of the line of sight flux of chemical species, and obtaining other information about the target volume, without introducing the spatial and temporal sampling errors that often dominate flux measurements made by systems employing separate instruments. Integration of DIAL and optical autocovariance HSRL signal processing functions in a single system also enables error correction in DIAL measurements for the variability of aerosol extinction and backscatter cross section across the sensed volume without incurring spatio-temporal sampling errors. Integration of optical autocovariance HSRL and double-edge etalon wind measurements and signal processing allows correction of the etalon wind measurements for errors introduced by changes in the spectral shape of the return due to changing aerosol to molecular backscatter mixing ratio.

Figure 3:
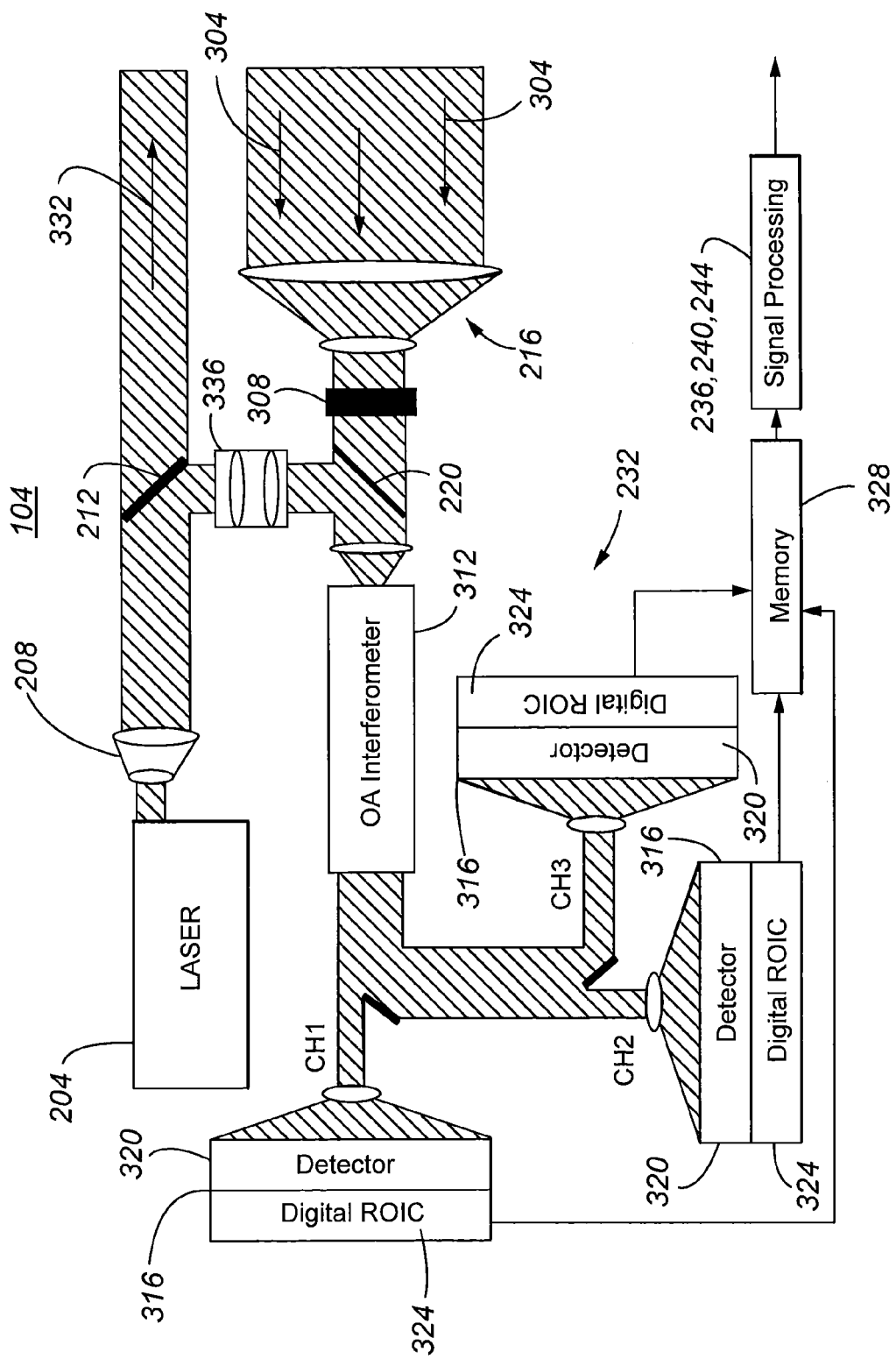
FIG. 3 is a depiction of components of an optical autocovariance receiver in accordance with embodiments of the present invention.

FIG. 3 is a depiction of components of an optical autocovariance receiver 232 and associated lidar system 104 components in accordance with embodiments of the present invention. The lidar system 104 shown in FIG. 3 is similar to the system 104 of FIG. 2, except that additional details of the optical autocovariance receiver 232 are included in FIG. 3, and the lidar system 104 of FIG. 3 does not include an Etalon receiver 228, a Raman receiver 248, a depolarization receiver 256, and processors and optical elements specific to those additional receivers. The lidar system 104 of the embodiment in FIG. 3 generally includes a telescope 216 to receive reflected photons 304. The telescope 216 directs the photons 304 through an optical bandpass filter 308. The filtered light is then provided to a an optical autocovariance (OA) interferometer 312. As can be appreciated by one of skill in the art, in the OA interferometer 312, the beam of received photons 308 is split into two beams, with one of the beams being directed along a first arm of the interferometer 312 and a second of the beams being directed along a second arm of the interferometer 312. In the second arm of the interferometer 312, the beam is sub-divided with each subdivision having a slightly different path length. The beams from the first and second arms are then recombined, and provided to detector assemblies 316. More particularly, each of the sub-divisions of the beam directed along the second arm of the interferometer comprises a channel, and each detector assembly 316 is provided with light corresponding to one of the channels. In the example optical autocovariance interferometer 312 illustrated in the figure, there are three channels. However, embodiments of the present invention are not limited to three channels. For example, an optical autocovariance interferometer 312 may incorporate four or more channels. Still other embodiments may incorporate two channels. In addition, the phase delay channels may be implemented by using waveplates, and the channels may all use the same beam path by implementing polarization multiplexing Each detector assembly 316 may include a detector 320 comprising a single pixel detector or a multiple pixel array. For example, if a multiple pixel detection array is included, the arrays may have M×M (e.g. 256×256) pixels. More particularly, each detector 320 may comprise a photo sensitive detector and electron multiplier. In addition, each detector 320 may include a digital readout integrated circuit 324. Moreover, the detector assemblies 316 may comprise photon counting detectors. The output from each detector 320 may be provided to a memory 328, and from memory 328 to a processor comprising the Doppler signal processor 236, where wind velocity and backscatter signal intensity profiles will be calculated. The processor may also comprise, separately or integrated with the Doppler signal processor 236, the HSRL signal processor 240 and/or the DIAL signal processor 244. As can be appreciated by one of skill in the art, the various processors 230, 236, 240, 244, 252, 260 can be implemented by various means, for example by a general purpose programmable processor executing program instructions, a controller executing firmware, and/or an application specific integrated circuit. Moreover, the processors can be implemented individually or in combination with one another.

The example lidar system 104 in FIG. 3 also provides a transmitting function, and thus is an example of a lidar transceiver. Accordingly, a single longitudinal mode laser or lasers 204 may be provided. In accordance with embodiments of the present invention, the laser produces substantially single frequency light with single pulse coherence length exceeding the interferometer optical path difference (OPD), but need not have the same single frequency on different shots. Light is generally sent out from the laser 204 in pulses, to be reflected from molecules and particles in the observation area 108, as a transmitted beam 332. In addition, the beam splitter 212 and sampling optics 336 are provided to direct light from the laser 204 to the OA interferometer 312, to provide the interferometer 312 with information regarding the optical autocovariance function (ACF) phase of the transmitted beam 324 (0-phase, 0-time sample). This information is used as a reference to enable measurement of the ACF phase shift experienced by the reflected light 304 to be determined.

Accordingly, the example lidar shown in FIG. 3 represents a basic lidar system 104 in accordance with embodiments of the present invention. However, as discussed elsewhere herein, for example in connection with FIG. 2, a lidar system 104 in accordance with embodiments of the present invention may include one or more receivers in addition to the optical autocovariance receiver 232. Moreover, whether or not receivers in addition to the optical autocovariance receiver are included, the optical autocovariance interferometer 312 of the optical autocovariance receiver 232 is present, in order to provide wind speed and range information in addition to at least one of HSRL information, DIAL information, information from an Etalon receiver 228, information from a Raman receiver 248, or information from a depolarization receiver 256.

Figure 4:
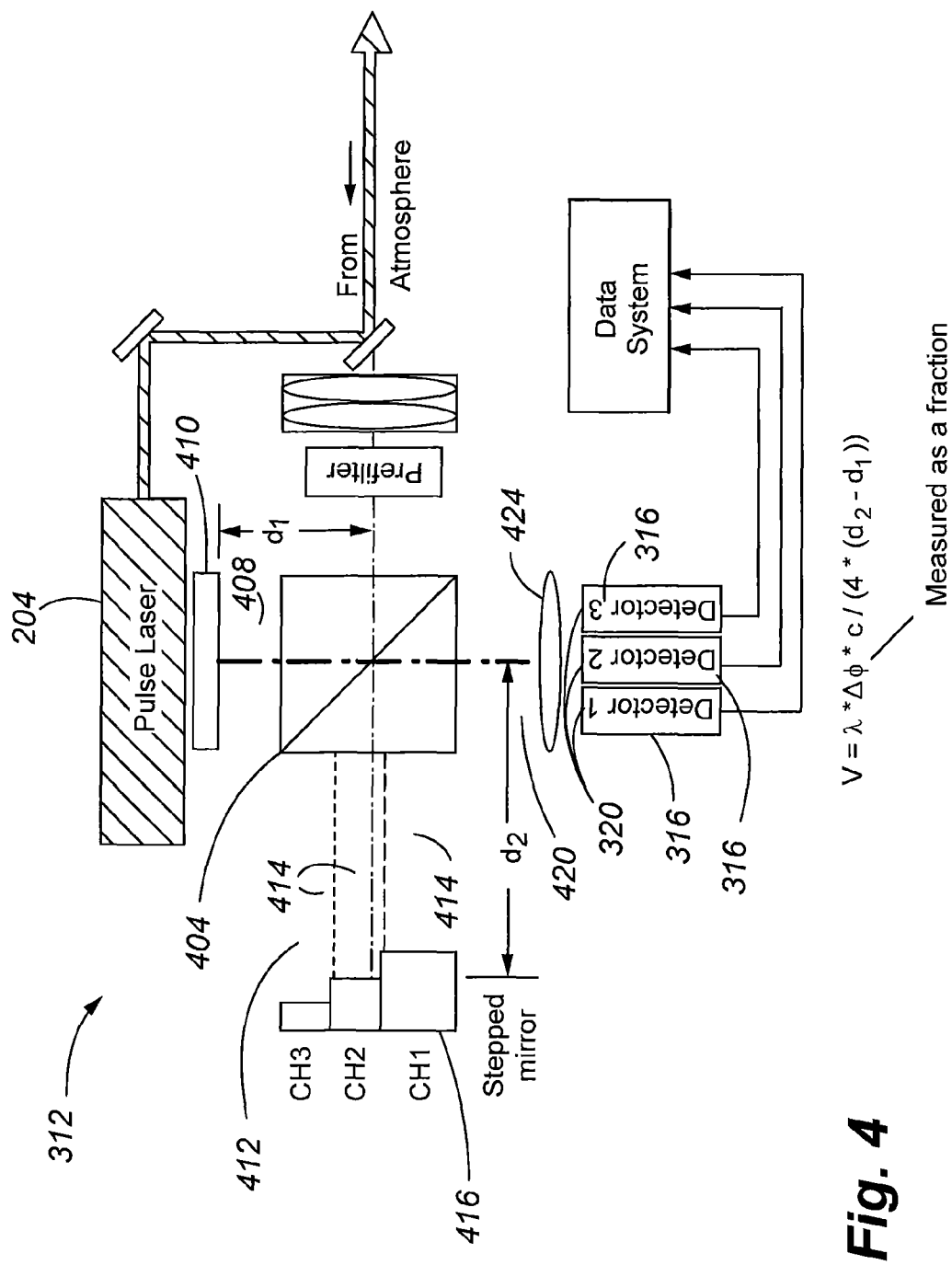
FIG. 4 is a depiction of details of an optical autocovariance receiver in accordance with embodiments of the present invention.

FIG. 4 illustrates aspects of an optical autocovariance interferometer 312 in accordance with embodiments of the present invention. In particular, the OA interferometer 312 includes a beam splitter 404 that splits received light reflected from the atmosphere 208 (or light from the laser 204) into a beam directed along a first arm 408 of the interferometer or a second arm 412 of the interferometer. Each of the arms 408, 412 have a nominal path length that is different from one another. In addition, the second arm 412 is sub-divided into a number of areas 414 by a stepped mirror 416. In particular, the stepped mirror provides each of the areas with a slightly different optical path length along the second arm 412. In general, one area is provided for each channel or detector 320.

Light directed along the first path 408 is reflected by a plane mirror 410 back through the beam splitter 404 to a detection arm 420. Similarly, light directed along the second arm 412 is reflected by the stepped mirror 416 back through the beam splitter 404 to the detection arm 420. The light is then passed through focusing optics 424 and focused onto the detector assemblies 316. At the beamsplitter 404, there is interference between light that was directed along the first arm 408 of the interferometer and light directed along the second arm 412 of the interferometer. The intensity of the combined interfered beams from arms 408 and arm 412 is focused on the detectors 320 of the detector assemblies 316 by a lens or optics 424. Moreover, based on the intensity of the light from corresponding pixels of the plurality of detector assemblies 316, the ACF phase of the detected light can be determined. Specifically, the change in ACF phase relative to the phase of the ACF light transmitted by the laser 204 can be determined, thus allowing the relative line of sight velocity of the particles and molecules in the observation area 108 that backscattered the received light to be determined. Another example of an optical autocovariance lidar using a stepped mirror suitable for inclusion in a lidar system 104 in accordance with embodiments of the present invention is disclosed in U.S. Pat. No. 7,359,057, the disclosure of which is incorporated herein by reference to the extent that it describes an operative optical autocovariance interferometer.

Figure 5:
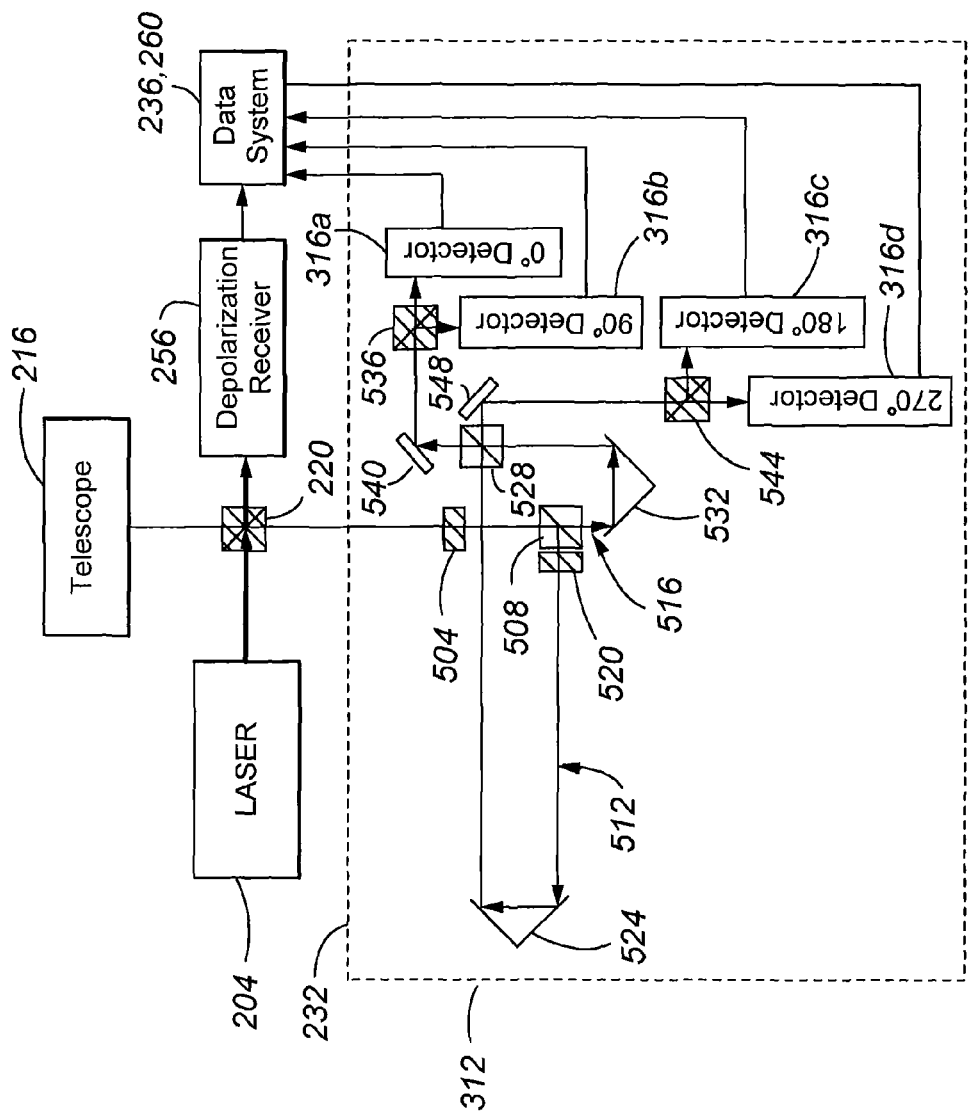
FIG. 5 is a depiction of details of another optical autocovariance receiver in accordance with embodiments of the present invention.

FIG. 5 illustrates aspects of an optical autocovariance interferometer 312 in accordance with other embodiments of the present invention. More particularly, the optical autocovariance interferometer 312 shown in FIG. 5 utilizes polarization multiplexing in order to obtain a plurality of differential delays in order to allow measurement of the phase shift of the optical autocovariance function experienced by reflected light collected by the telescope 216. In particular, the embodiment illustrated in FIG. 5 allows for different measurements of the intensity of ACF of the returned signal at different relative phase delays to be determined. Using the disclosed architecture, additional detectors for measuring the intensity of a return signal at different points along the optical ACF of the returned signal and/or to accommodate simultaneous measurement of the optical ACF from the return signals of different wavelengths can also be included. The optical autocovariance lidar 312 comprises some or all of an optical autocovariance receiver 232 in accordance with embodiments of the present invention. Randomly polarized light collected by the telescope 216 is provided to the polarizing beam splitter 220, which passes the light collected by the telescope 216 as linearly polarized light to the optical autocovariance interferometer 312. In addition, the polarizing beam splitter 320 functions to reflect a sample of the light from the laser 204, which comprises a linearly polarized zero phase reference signal. The polarizing beam splitter 220 can also function to provide a signal to the depolarization receiver 256, although as noted, a depolarization receiver 256 is not required.

Linearly polarized light from the polarizing beam splitter 220 is passed through a half wave plate 504, which rotates the polarization of the light from the polarizing beam splitter 220 by 45°. Other well known methods can be used to perform the rotation of the polarization states, for example, physical rotation of the optical path. Next, a first non-polarizing 50% beam splitter 508 divides the light, and directs one half of the light along a long arm 512 and the other half of the light along a short arm 516 of the optical autocovariance interferometer 312. The light in each arm comprises orthogonal polarizations, each containing one half the light directed to the respective arm. The light directed along the long arm 512 can be passed through a quarter wave plate 520 aligned so as to shift the phase of the light in one of the polarizations propagating in the long arm 512 by 90° with respect to the other polarization in that arm. As can be appreciated by one of skill in the art after consideration of the present disclosure, alternatively the quarter wave plate can be positioned so that the phase of one of the polarizations of light directed along the short arm 516 is shifted by 90°. At the end of the long arm 512 of the OA interferometer 312 is a first cube corner 524 that directs the light towards a second non-polarizing 50% beam splitter 528. A second cube corner 532 at the end of the short arm 516 of the OA interferometer 312 directs the light in the short arm 516 towards a face of the second non-polarizing 50% beam splitter 528 that is orthogonal to the face of the second non-polarizing 50% beam splitter 528 to which the light from the long arm 512 is directed. Accordingly, the light from the two arms, 512, 516 of the OA interferometer 312 mixes and interferes at the second non-polarizing 50% beam splitter 528.

A first half of the light received from the arms 512, 516 is reflected by the second non-polarizing 50% beam splitter 528 to a second polarizing beam splitter 536. As shown in the figure, light may be directed to the second polarization beam splitter 536 by a mirror 540. The second polarizing beam splitter 536 passes light having a first polarization to a 0° detector assembly 316a, and reflects light having a second polarization, orthogonal to the first polarization, to a 90° detector assembly 316b. The light passed by the second non-polarizing 50% beam splitter 528 is received by a third polarization beam splitter 544. As shown in the figure, the light passed by the second non-polarizing 50% beam splitter 528 may be directed to the third polarization beam splitter 544 by a second mirror 548. The third polarization beam splitter 544 reflects light having a particular polarization to a 180° detector assembly 316c, and passes light having an orthogonal polarization to a 270° detector assembly 316d. The intensity of the signals at the detector assemblies 316a-d is provided to the data system or Doppler signal processor 236. Said signals represent relative phase samples of the optical ACF of the input light with the angular denotations representing approximate relative phase spacing of the samples in that autocovariance space. Other optical ACF phase spacings are feasible, providing they are known or measured, while it is advantageous to spread the samples equally over a substantial fraction of a cycle of the ACF in order to maximize the unambiguous velocity range of the lidar system. More particularly, the Doppler signal processor 236 may determine the phase shift of the optical ACF of the light collected by the telescope 216 from the ratios of the detected intensities provided by the detector assemblies 316a-d. In addition, where a depolarization receiver 256 is included, the data system may further comprise the depolarization signal processor 260.

A lidar system 104 in accordance with embodiments of the present invention that includes a polarizing beam splitter 220 that receives light transmitted by the laser 204 can provide functions and advantages in addition to those already mentioned. For example, the sample of the outgoing laser light reflected from the polarizing beam splitter 220 into or towards the optical autocovariance receiver 232 enables the reference autocovariance function phase measurement to be performed without requiring additional optics in the path. This sample of the outgoing laser light has the orthogonal polarization to the input light collected by the telescope 216 that is passed through the polarizing beam splitter 220. Accordingly, the autocovariance function is shifted by a fixed amount (in the illustrated embodiment, 180°) from the needed reference.

Figure 6:
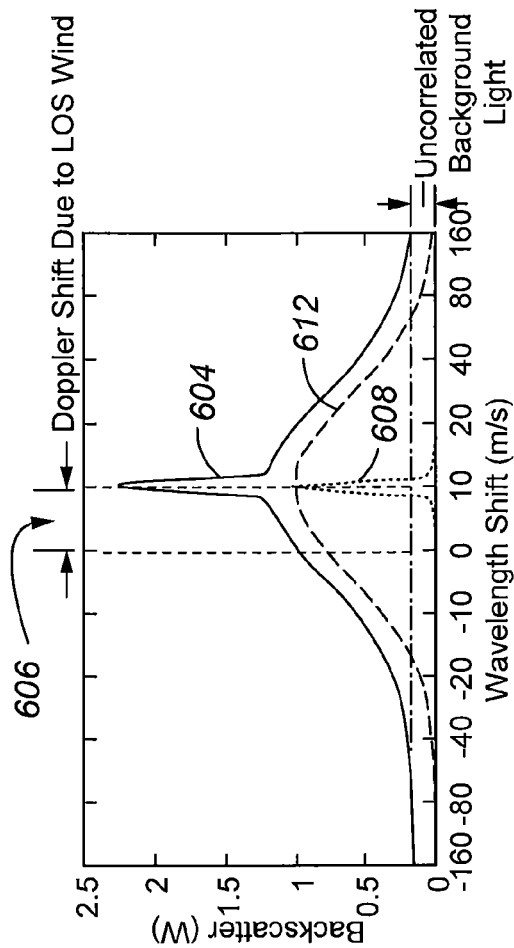
FIG. 6 shows a typical spectral distribution of light from a monochromatic laser backscattered from the atmosphere.
Figure 7:
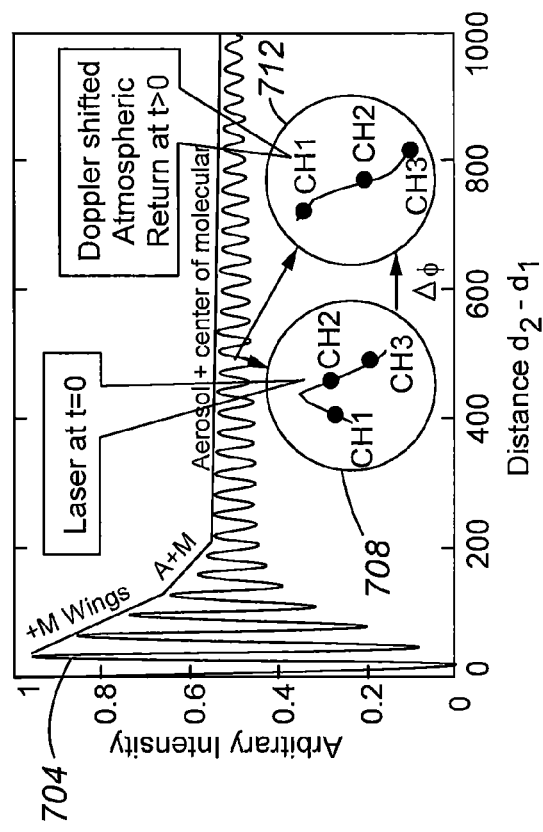
FIG. 7 depicts the measurements obtained by different detectors of an optical autocovariance receiver in accordance with embodiments of the present invention.

FIG. 6 shows the typical spectral distribution of light backscattered from the atmosphere 604 from a monochromatic laser illumination showing the Doppler shift 606 of the center of the return spectrum from both aerosols 608 and molecules 612. The molecular return 612 is spectrally wider than the aerosol return 608 because molecules also move randomly with thermal velocities while the more massive aerosols move randomly with much slower Brownian motions. FIG. 7 depicts the measurements obtained by the different detector assemblies 316 corresponding to the different channels of then OA interferometer 312. More particularly, FIG. 7 shows the optical ACF 704 of the typical spectrum shown in FIG. 6 as a function of the optical path difference between the two arms of the interferometer. It can be seen in the insets 708, 712 in FIG. 7 that the sub-division of the light in the interferometer of fixed OPD that produces the aforementioned different samples of the optical ACF (here indicated as the channels CH1, CH2, and CH3) can be used to find the shift ($\Delta\phi$) in the phase of the ACF function between the 0-velocity 0-range sample of the light produced by the laser 204 (see inset 708) and the ACF of the light backscattered from the atmosphere (see inset 712). Be it noted that the shape of the ACF is substantially a sine function, and that least squares or other fitting of the measured optical ACF samples with known phase spacing leads to substantial reduction in the uncertainty of the ACF phase determination. Best performance of the fitting process results from equalization of the transmission losses and compensation for residual channel cross talk that may be accomplished by a calibration step using the zero-time samples from the laser, either between or during data acquisitions. Furthermore, the offset O and the amplitude A of the resolved component of the optical ACF determined from a sine fit to the optical ACF samples comprise the signal components useful to simultaneous HSRL retrieval. O is proportional to the intensity of the molecular portion of the return spectrum, while A is proportional to the aerosol dominated center of the return spectrum. Accordingly, A and O represent different linear combinations of the backscatter intensity fractions from aerosol and from molecules as needed to implement HSRL retrieval. A significant advantage of implementing an HSRL using the optical autocovariance technique over other methods is that the retrieval is independent of the Doppler shift induced by wind velocity.

Figure 8:
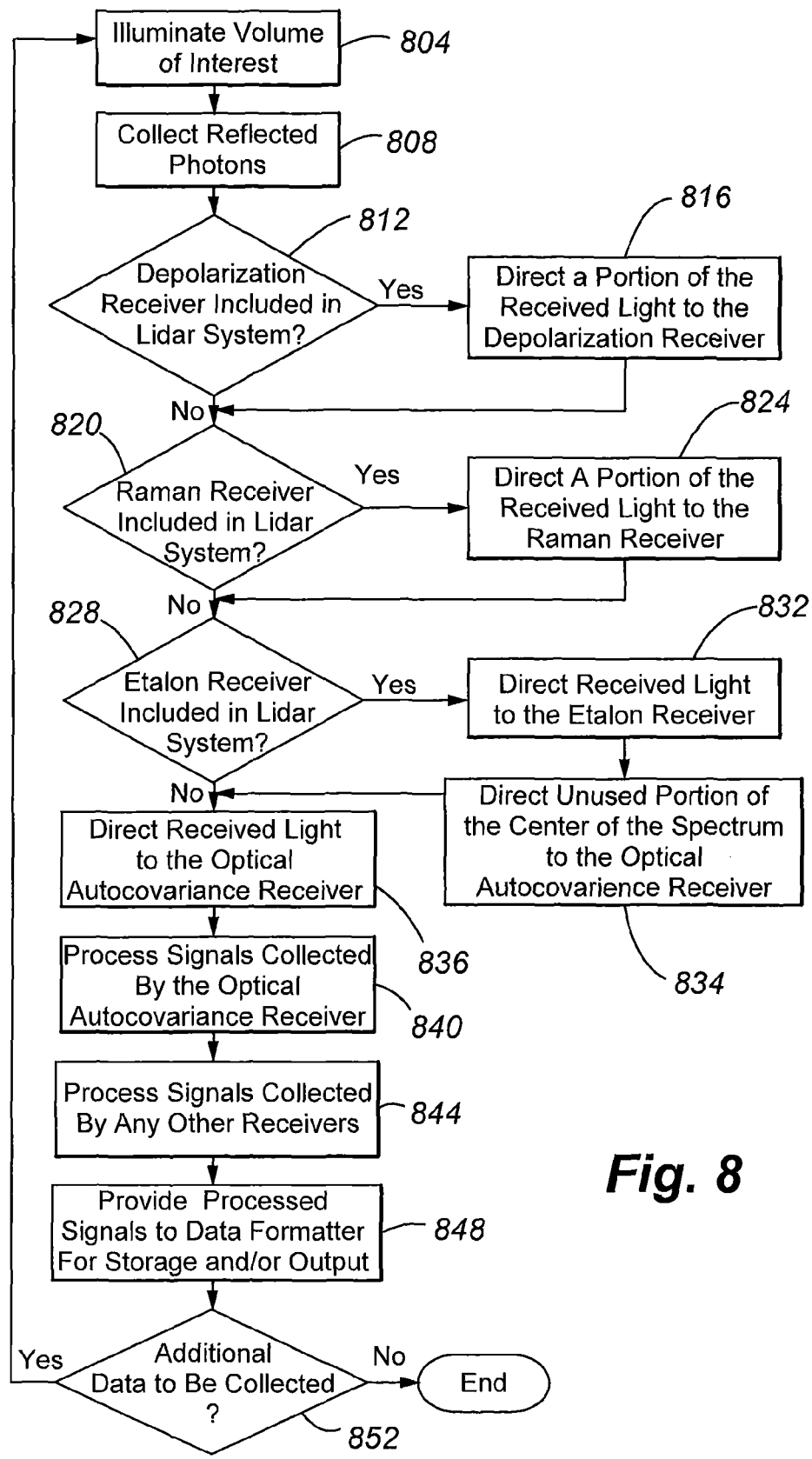
FIG. 8 is a flow chart illustrating aspects of the operation of a lidar in accordance with embodiments of the present invention.

FIG. 8 is a flow chart depicting aspects of the implementation and operation of a lidar system 104 in accordance with embodiments of the present invention. Initially, at step 804, the volume or target of interest is illuminated (step 804). Illumination of a volume of interest can include controlling a laser 204 to provide output at a selected wavelength and directing that output to the target or volume of interest in the atmosphere via the beam shaping optics 208. In addition, a sample of the output from the laser may be directed to the optical autocovariance receiver 232 as a reference.

Photons from the laser 204 that are reflected back to the lidar system 104 by the target or volume of interest are collected (step 808). The collection of reflected photons may be performed by the telescope 216. Moreover, a single telescope 216 may operate to provide collected photons to receivers included in the lidar system 104.

If a depolarization receiver 256 is included in the lidar system 104 (step 812) a portion of the received light is directed to the depolarization receiver 256 (step 816). For example, by a polarizing beam splitter 220. More particularly, the orthogonal polarization components of the received spectrum can be directed to the depolarization receiver 256 by the polarizing beam splitter 220. The non-polarized components, which are passed to the optical autocovariance receiver 232, are proportional to the sum of the corresponding optical autocovariance receiver 232 detector signals. The depolarization ratio is calculated as the quotient of the depolarization signal divided by the sum of the depolarized and non-depolarized components (all corrected for transmission losses), allowing depolarization lidar profiling simultaneously with wind profiling, without sacrifice of performance in any of the measurements.

If a Raman receiver 248 is included in the lidar system 104 (step 820) a portion of the received light is directed to the Raman receiver 248 (step 824). The portion of the received light may be directed to the Raman receiver by the dichroic mirror 224. The collection of the Raman signal can be facilitated by choosing the wavelength generated by the laser 204 to be in the range from the UV to near IR wavelengths. The combination of the optical autocovariance receiver 232 lidar with the Raman receiver 248 lidar is mutually advantageous, and enables the use of a common laser for diverse measurements without loss of performance for either measurement, because the return signals are spectrally separable. In addition, the common measurement path simplifies coordination of spatial and temporal sampling, reducing measurement errors and system complexity. Raman signals gathered for inhomogenously mixed chemical species (e.g., hydrocarbons, $O_3$, $SO_x$, $NO_x$, etc.) can be simultaneously measured with additional appropriate filters in the Raman receiver 248. Where the Raman receiver 248 is incorporated into a lidar system 104 that also incorporates a depolarization receiver 256, the Raman receiver 248 may be provided with non-depolarized components of the returned light passed by the polarizing beam splitter 220, and then reflected to the Raman receiver 248 by the dichroic mirror 224. Accordingly, a lidar system 104 that incorporates an optical autocovariance receiver 232 and a Raman receiver 248 can also include a depolarization receiver 256, without sacrificing the performance of any of the measurements made by the included receivers.

If an Etalon receiver 228 is included in the lidar system 104 (step 828) received light is directed to the Etalon receiver 228 (step 832). As can be appreciated by one of skill in the art, the Etalon receiver 228 can measure the mean Doppler shift of the center of the Doppler broadened molecular backscatter spectrum to obtain wind speed by using, for example, the doubled-edge direct detection wind lidar technique. In this approach, the light rejected by the Etalon receiver 228, which comprises primarily the center of the backscatter spectrum, can then be passed to the optical autocovariance receiver 232 (step 834) to determine the precise optical frequency of the return light, in order to measure the Doppler shift of the central frequency due to relative motion from the aerosol dominated portion of the backscatter. Because the aerosol backscatter is not Doppler broadened, it can be used, when present, to produce much more precise velocity estimates. The combination of an etalon receiver with an optical autocovariance wind lidar receiver enables optimization of each receiver for the relevant backscatter component leading to improved system precision, measurement availability, and measurement precision. Where the lidar system 104 includes other receivers in addition to the Etalon receiver 228 and the optical autocovariance receiver 232, the Etalon receiver 228 may be provided with reflected light collected by the telescope 216 via the polarizing beam splitter 220 and the dichroic mirror 224.

At step 836, light received at the telescope 216 is directed to the optical autocovariance receiver 232. Where no additional receivers are included in the lidar system 104, for example where the lidar system includes the optical autocovariance receiver 232 and a Doppler signal processor 236 in combination with at least one of an HSRL signal processor 240 and a DIAL signal processor 244, the optical autocovariance receiver 232 may be provided from the telescope 216 directly. Alternatively, the optical autocovariance receiver 232 may be provided with light collected by the telescope 216 via an element that also operates to provide a sample of the light transmitted by the laser 204 for calibration. Accordingly, even where no receivers other than the optical autocovariance receiver 232 are included in the lidar system 104, the light from the telescope 216 may be provided to the OA receiver 232 via a polarizing beam splitter 220 or other element. As noted above, where the lidar system 104 also includes a depolarization receiver 256, the polarizing beam splitter 220 provides depolarized return components to the depolarization receiver 256. Also as previously described, where the lidar system 104 includes a Raman receiver 248, light provided to the optical autocovariance receiver 232 may be passed through a dichroic mirror 224 that operates to provide some of the received light to the Raman receiver 248. In addition, where an Etalon receiver 228 is incorporated into the lidar system 104, collected light may first be processed by the Etalon receiver 228 before being passed to the optical autocovariance receiver 232. The signals collected by the optical autocovariance receiver 232 from the collected light provided to that receiver 232 can then be processed (step 840). More particularly, the optical autocovariance receiver 232 includes at least three detector assemblies 316 that are operable to determine the intensity of a received signal at different points along some or all of the optical ACF of that signal. In particular, the intensity measurements allow the optical frequency shift of the return signal that has been collected by the telescope 216 to be determined, and thus provides the Doppler shift due to wind in the atmosphere experienced by the signal transmitted by the laser 204 relative to the lidar system 104. This processing may be performed by a Doppler signal processor 236.

In addition, information collected by the optical autocovariance receiver 232 may be processed to obtain other information. For instance, by operating the laser 204 at more than one wavelength, either simultaneously or sequentially, where those wavelengths are chosen to coincide with an absorption line of a specific surface coating or atmospheric component, chemical species measurements can also simultaneously be obtained using the differential absorption lidar method. Moreover, because the optical autocovariance receiver 232 allows frequency hopping without affecting the performance of the OA receiver 232 as a wind lidar, provided the zero phase sample is measured and the Doppler shift is determined from the differential optical autocovariance function phase shift between the zero phase measurement and the return, composition measurements using the DIAL method and wind measurements can be performed simultaneously.

Additionally or alternatively, a high spectral resolution lidar processor 240 can be provided with signals from the OA receiver 232 to retrieve HSRL profiles of calibrated aerosol optical properties, such as particle extinction cross section, backscatter cross section, and backscatter phase function. Therefore, by providing a DIAL signal processor 244 and/or an HSRL signal processor 240, information regarding characteristics of a volume of interest or target can be obtained from signals provided by the optical autocovariance receiver 232, in addition to relative wind speed.

Where receivers in addition to the OA receiver 232 are included in the lidar system 104, signals from those receivers are also processed (step 844). For example, signals obtained by a depolarization receiver 256 may be processed by a depolarization signal processor 260. Signals collected by a Raman receiver 248 may be processed by a Raman signal processor 252. Signals collected by an Etalon receiver 228 may be processed by an Etalon signal processor 230.

Processed signals from signal processors included in the lidar system 104 can be provided to the data formatter 234 for storage and/or output (848). For example, where the lidar system 104 is provided as part of a satellite 100 or other remote system, the data formatter 234 may store data until it can be transmitted to a ground station or other data center.

At step 852, a determination may be made as to whether additional data is to be collected by the lidar system 104. If additional data is to be collected, the process may return to step 804. Otherwise, the process may end.

In accordance with embodiments of the present invention, background light can be subtracted from the optical autocovariance receiver 232 signal by measuring the temporally decorrelated signal at the individual detectors before or after the atmospheric signal return of the light transmitted from the laser 204 that is collected by the telescope 216 is provided to the optical autocovariance receiver 232. Moreover, the subtraction may be performed before autocovariance function processing. In accordance with further embodiments of the present invention, orbital velocity compensation can be accomplished during processing of receive signals. In particular, the aliasing property of the optical autocovariance wind lidar can be used to perform orbital velocity compensation by software subtraction of the known line of sight orbital velocity. Accordingly, embodiments of the present invention allow orbital velocity compensation to be performed, without requiring specialized, high precision hardware tuners on the optical frequency of the local oscillator laser typically required to keep the signal within reasonable electronic bandwidths for coherent detection Doppler systems or the fast settling piezoelectric transducers driving the Etalons in double edge direct detection systems required to keep the signal in the wavelength gap between the bandpass functions.

Although particular embodiments of lidar systems 104 in accordance with embodiments of the present invention have been illustrated and described, it should be appreciated that other embodiments are possible. For instance, a lidar system 104 in accordance with an embodiment of the present invention incorporates an optical autocovariance receiver 232, a Doppler signal processor 236 for obtaining wind speed information, and at least one of a high spectral resolution lidar signal processor 240 and a differential absorption lidar signal processor 244 that receive signal information from the optical autocovariance receiver 232. In accordance with other embodiments, the optical autocovariance receiver 232 and the Doppler signal processor 236 are provided in combination with one or more additional receivers. Examples of the different receivers that can be included in addition to the optical autocovariance receiver 232 include an Etalon receiver 228, a Raman receiver 248, and a depolarization receiver 256. Each receiver may be associated with one or more signal processors. Alternatively, signal processing with respect to signals obtained by the various receivers can be performed by a single supporting processor or some other number of processors. Accordingly, the various processors can be implemented as different algorithms or processes running on, for example, one or more shared processors, controllers, or computers. In addition, optical elements, such as polarizing beam splitters, non-polarizing beam splitters, dichroic mirrors and plane mirrors may be included, to enable photons collected by a common telescope 216 to be directed to the various receivers 228, 232, 248 and/or 256. In addition, provision is made to provide a sample of a signal generated by a laser 204 to included receivers as necessary for calibration or as a reference signal.

In accordance with still other embodiments of the present invention, detector assemblies included in the optical autocovariance receiver 232 can include a single pixel, or multiple pixels, for example as part of an imaging lidar. Moreover, implementation of an optical autocovariance receiver is not limited to the types described herein. In addition, various modifications can be incorporated. For example, field widening optics can be incorporated into the optical autocovariance receiver. Field widening optics are particularly desirable where the detectors 320 of the detector assemblies 316 contain multiple pixels, or to enable systems tolerant to misalignment between the receiver and transmitter optic axes.

In accordance with still other embodiments, a lidar system 104 can include receivers that can optionally be provided with photons collected by the telescope 216. For example, an Etalon receiver 228 may, in a first mode of operation, be provided with photons collected by the telescope 216, and may then pass some or all of those photons to the optical autocovariance receiver 232. In a second mode of operation, the Etalon receiver 228 may be switched out of the optical path, such that photons collected by the telescope 216 are passed to the optical autocovariance receiver 232, without first having passed through the Etalon receiver 228. Beam splitters for diverting photons to a Raman receiver 248 and/or a depolarization receiver 256 can also be operated to selectively provide collected light to the associated receivers. Accordingly, operation of a lidar system 104 can, in at least some embodiments, be controlled so that only desired receivers, even if otherwise included in the lidar system 104, are operated at a particular point in time.

The foregoing discussion of the invention has been presented for purposes of illustration and description. Further, the description is not intended to limit the invention to the form disclosed herein. Consequently, variations and modifications commensurate with the above teachings, within the skill or knowledge of the relevant art, are within the scope of the present invention. The embodiments described hereinabove are further intended to explain the best mode presently known of practicing the invention and to enable others skilled in the art to utilize the invention in such or in other embodiments and with various modifications, required by the particular application or use of the invention. It is intended that the appended claims be construed to include alternative embodiments to the extent permitted by the prior art.

What is claimed is:

1. A lidar system, comprising:
   a telescope;
   an optical autocovariance receiver, wherein the optical autocovariance receiver is provided with an input signal by the telescope;
   a Doppler signal processor, wherein an output from sensors included in the optical autocovariance receiver is provided to the Doppler signal processor; and
   a physical property sensor, wherein the physical property sensor is provided with an input signal by the telescope.

2. The system of claim 1, wherein the physical property sensor comprises at least one of a differential absorption lidar and signal processor and a high spectral resolution lidar and processor determining aerosol optical properties, and wherein the output from sensors included in the optical autocovariance receiver is provided to the at least one of a differential absorption lidar signal processor and a high spectral resolution lidar processor.

3. The system of claim 1, wherein the physical property sensor comprises a differential absorption lidar signal processor determining chemical composition and a high spectral resolution lidar processor determining aerosol optical properties, and wherein the output from sensors included in the optical autocovariance receiver is provided to the differential absorption lidar signal processor and the high spectral resolution lidar processor.

4. The system of claim 1, further comprising:
   a Raman receiver, wherein the Raman receiver is provided with an input signal by the telescope.

5. The system of claim 4, further comprising:
   a dichroic mirror, wherein a first portion of an input signal from the telescope is passed by the dichroic mirror for provision to the optical autocovariance receiver, and wherein a second portion of an input signal from the telescope is directed by the dichroic mirror to the Raman receiver.

6. The system of claim 1, further comprising:
   a depolarization receiver, wherein the depolarization receiver is provided with an input signal by the telescope.

7. The system of claim 6, further comprising:
   a polarizing beam splitter, wherein a first portion of an input signal from the telescope is passed by the polarizing beam splitter for provision to the optical autocovariance receiver, and wherein a second portion of an input signal from the telescope is directed by the polarizing beam splitter to the depolarization receiver.

8. The system of claim 1, further comprising:
   an Etalon receiver, wherein the Etalon receiver is provided with an input signal by the telescope.

9. The system of claim 1, further comprising:
   a laser, wherein a sample of an output from the laser is provided to the optical autocovariance receiver.

10. A lidar system, comprising:
    a laser;
    an optical autocovariance receiver;
    a first optical element operable to provide a sample of a signal generated by the laser to the optical autocovariance receiver;
    a telescope, wherein the telescope is operable to provide collected photons to the optical autocovariance receiver;

a Doppler signal processor operable to calculate a relative wind speed from information provided by the optical autocovariance receiver;

at least one of:
- a high spectral resolution lidar signal processor operable to determine characteristic of a target volume from information provided by the optical autocovariance receiver;
- a differential absorption lidar signal processor operable to determine a characteristic of a target volume from information provided by the optical autocovariance receiver;
- an etalon receiver operable to determine a characteristic of a target volume, wherein the telescope is operable to provide collected photons to the etalon receiver;
- a Raman receiver operable to determine a characteristic of a target volume, wherein the telescope is operable to provide collected photons to the Raman receiver;
- a depolarization receiver operable to determine a characteristic of a target volume, wherein the telescope is operable to provide collected photons to the depolarization receiver.

11. The system of claim 10, wherein the lidar system includes a high spectral resolution lidar signal processor operable to determine a characteristic of a target volume from information provided by the optical autocovariance receiver.

12. The system of claim 10, wherein the lidar system includes a differential absorption lidar signal processor operable to determine a characteristic of a target volume from information provided by the optical autocovariance receiver.

13. The system of claim 12, wherein the differential absorption lidar signal processor is in communication with a laser control, wherein the laser includes one or more lasers, and wherein the laser control causes signals of different wavelengths to be transmitted from the one or more lasers.

14. The system of claim 10, wherein the lidar system includes an etalon receiver operable to determine a characteristic of a target volume, wherein the telescope is operable to provide collected photons to the etalon receiver.

15. The system of claim 14, wherein photons collected by the telescope pass to the etalon receiver before at least some of those photons are provided to the optical autocovariance receiver.

16. The system of claim 10, wherein the lidar system includes a Raman receiver operable to determine a characteristic of a target volume, wherein the telescope is operable to provide collected photons to the Raman receiver.

17. The system of claim 10, wherein the lidar system includes a depolarization receiver operable to determine a characteristic of a target volume, wherein the telescope is operable to provide collected photons to the depolarization receiver via a polarizing beam splitter.

18. The system of claim 10, wherein the optical autocovariance receiver includes at least two photon-counting detectors.

19. The system of claim 10, wherein the optical autocovariance receiver includes at least three multiple pixel detector arrays.

20. A method for obtaining information about a target volume, comprising:
- transmitting light to a target volume;
- collecting photons reflected from the target volume using a telescope, wherein the collected photons include photons transmitted to the target volume;
- providing at least some of the photons reflected from the target volume and collected by the telescope to a first receiver, wherein the first receiver is an optical autocovariance receiver;
- determining a first characteristic of the target volume, wherein the first characteristic includes an optical frequency of the photons reflected from the target volume and collected by the telescope using information provided by the optical autocovariance receiver, and wherein the optical frequency of the photons reflected from the target volume and collected by the telescope is used to determine a relative wind speed within the target volume;
- determining a second characteristic of the target volume, wherein the second characteristic is different than the first characteristic.

21. The method of claim 20, wherein the second characteristic is calculated from information provided by the optical autocovariance receiver.

22. The method of claim 20, further comprising:
- providing at least some of the photons reflected from the target volume and collected by the telescope to a second receiver, wherein the second characteristic is calculated from information provided by the second receiver.

23. The method of claim 20, further comprising:
- providing a sample of light transmitted by the laser to the target volume of the optical autocovariance receiver;
- taking a reference autocovariance function phase measurement from the sample, wherein the autocovariance function is shifted by a fixed amount to obtain the reference autocovariance function.

24. The system of claim 1, wherein the optical autocovariance receiver includes:
- a beam splitter, wherein the beam splitter is operable to split light received as an input to the autocovariance receiver into first and second beam paths;
- a first arm, wherein the first arm has a first nominal path length, and wherein the first beam path includes the first arm;
- a second arm, wherein the second arm has a second nominal path length, wherein the second arm is sub-divided into at least first, second and third areas, and wherein the second beam path includes the second arm;
- at least first, second and third detectors, wherein the first detector is located to receive light from the first area and the first arm, wherein the second detector is located to receive light from the second area and the first arm, and wherein the third detector is located to receive light from the third area and the first arm.

25. The system of claim 10, wherein the sample of a signal generated by the laser and provided to the optical autocovariance receiver includes a spectral calibration signal.

* * * * *

UNITED STATES PATENT AND TRADEMARK OFFICE
CERTIFICATE OF CORRECTION

| | |
|---|---|
| PATENT NO. | : 8,077,294 B1 |
| APPLICATION NO. | : 12/357251 |
| DATED | : December 13, 2011 |
| INVENTOR(S) | : Grund et al. |

It is certified that error appears in the above-identified patent and that said Letters Patent is hereby corrected as shown below:

In Claim 2
Column 16,
Line 19, delete the first and third instances of "and".

Signed and Sealed this

Seventh Day of February, 2012

David J. Kappos
*Director of the United States Patent and Trademark Office*